United States Patent [19]
Maxfield et al.

[11] Patent Number: 5,614,825
[45] Date of Patent: Mar. 25, 1997

[54] MAGNETIC FLUX LEAKAGE INSPECTION APPARATUS WITH SURFACE-RESPONSIVE SENSOR MOUNTING

[75] Inventors: Bruce W. Maxfield, Oakland; Pamela C. Fitzgerald, Berkeley, both of Calif.

[73] Assignee: Industrial Sensors and Actuators, San Leandro, Calif.

[21] Appl. No.: 345,901

[22] Filed: Nov. 28, 1994

[51] Int. Cl.$^6$ .......................... G01R 33/12; G01N 27/72
[52] U.S. Cl. .......................... 324/242; 324/235; 324/262
[58] Field of Search ........................... 324/235, 238–243, 324/262

[56] References Cited

U.S. PATENT DOCUMENTS

| | | | |
|---|---|---|---|
| 2,313,729 | 3/1943 | Barnes . | |
| 4,041,379 | 8/1977 | Karlsson | 324/37 |
| 4,258,319 | 3/1981 | Shimada et al. | 324/226 |
| 4,510,447 | 4/1985 | Moyer | 324/225 |
| 4,704,580 | 11/1987 | Moake et al. | 324/242 |
| 4,710,712 | 12/1987 | Bradfield et al. | 324/227 |
| 4,814,705 | 3/1989 | Saunderson | 324/238 |
| 5,279,160 | 1/1994 | Koch | 324/262 |

FOREIGN PATENT DOCUMENTS

| | | |
|---|---|---|
| 1567167 | 5/1980 | United Kingdom . |
| WO9316380 | 8/1993 | WIPO . |

OTHER PUBLICATIONS

Wiegant, "Automated NDT of Storage Tank Bottoms," Contribution to the KINT–BANT Symposium, Sep. 8–9, 1988, Antwerp, Belgium.
Nestleroth, "A Review of Magnetic Flux Leakage Technology for the In–Line Inspection of Gas Transmission Lines," International Conference on Pipeline Reliability, Jun. 2–5, 1992, Calgary, Alberta, Canada, pp. IV–5–1 to IV–5–12.
Dobmann, "Magnetic Leakage Flux Techniques in NDT, A State-of-the-Art Survey of the Capabilities for Defect Detection and Sizing," in *Electromagnetic Methods of NDT*, W. Lord, ed., Gordon and Breach, 1985, pp. 71–95.
Stanley, "An Overview of the Latest Magnetic NDE Methods," prior to Nov. 1994.

*Primary Examiner*—Walter E. Snow
*Attorney, Agent, or Firm*—Elliot B. Aronson

[57] ABSTRACT

Magnetic flux leakage inspection apparatus systems with independently suspended magnetic sensor blocks. The apparatus includes a magnet and a sensor assembly. The magnet is disposed over a surface of a magnetizable material under inspection for inducing magnetic flux in the material, and the sensor assembly is disposed in a predetermined inspection position over the surface for detecting magnetic flux leakage from the material that may indicate a magnetic anomaly in the material. The magnet and sensor assembly are moved along over the surface while the sensor assembly scans for magnetic leakage flux. The sensor assembly is formed with one or more independently suspended sensor blocks, each block including a plurality of sensors rigidly held in the block for detecting magnetic flux leakage. Each sensor block is independently mounted to permit the block to move perpendicular to the surface under inspection during the course of measurement as the sensor assembly and the surface are moved in scanning relation to one another. To avoid contamination of the measurement results by the normally present parallel flux leakage components, each block is subject to stringent constraints on the permitted departures of the perpendicular movement from perpendicularity, that is, on the amount by which the block may tilt as it undergoes its perpendicular movement. Each of the one or more blocks may be disposed to ride on the surface of the material under inspection, and each block may then undergo perpendicular movement independent of any other block in response to variations of the surface encountered in the course of inspection without causing undesirable magnetic field measurements to be mixed into the detected signal that would otherwise mask the much weaker desired signal indicative of magnetic anomalies.

24 Claims, 7 Drawing Sheets

MAGNETIC FLUX LEAKAGE INSPECTION APPARATUS WITH SURFACE-RESPONSIVE SENSOR MOUNTING

BACKGROUND OF THE INVENTION

The present invention relates generally to apparatus for the detection and measurement of magnetic anomalies in magnetic materials and is more particularly directed to apparatus for detecting magnetic flux leakage such as used for inspecting for defects in the bottoms of chemical and petroleum storage tanks or in tubing such as used in oil and gas wells.

The problems of detecting defects in ferromagnetic materials may be illustrated with reference to chemical and petroleum storage tanks. These tanks face gradual and continual deterioration due to the harsh chemical environment both outside and within the vessel. The steel walls of a tank are subject to corrosion, pitting, and other chemical and physical processes that can cause localized damage to the walls. Such localized damaged regions can develop into leaks or in extreme cases can lead to rupture of the tank. The tank bottom is exposed to corrosion or similar damage from the underside as well as from the top side. A tank typically rests on sand, gravel, crushed limestone, clay or similar base of varied composition. When the tank is filled, the bottom flexes and presses into the material under the weight of the contents. When the tank is then emptied, the bottom rises causing air and moisture to be drawn in, which accelerates the underside deterioration process.

To guard against environmentally damaging leaks or other tank failure, tank bottoms should be inspected periodically for early signs of damage conditions that may result in leakage. The underside of the tank bottom of course is inaccessible and thus cannot be inspected directly. One popular form of inspection apparatus looks for magnetic anomalies caused by local damage to the steel tank bottom. This apparatus includes one or more strong permanent magnets or electromagnets that induce a magnetic field within the steel plate forming the tank bottom that in effect locally magnetizes the plate. When the local region of the plate under the magnet is free of defects, it produces an induced magnetic flux of a known form that is highly regular. Localized defects from corrosion, pitting and the like produce irregularities in the highly regular form of the flux pattern that "leak out" of the steel plate. The irregularities in the otherwise regular flux pattern may be detected by sensors in the inspection apparatus positioned just above the plate surface, and this is so even if the defect producing the magnetic anomaly is on the inaccessible underside of the plate. In this way, detecting a magnetic anomaly signals the site of a possible defect in the steel bottom. Such apparatus is disclosed, for example, in U.S. Pat. No. 4,814,705 of Saunderson.

Although magnetic flux leakage methods have proved useful for detecting the presence of magnetic anomalies, the known magnetic flux leakage inspection devices intended for use in the field are not very precise. It has turned out to be difficult, cumbersome or expensive to apply magnetic flux leakage methods in the field for determining the detailed characteristics of magnetic anomalies with any quantitative precision. It would of course be useful to make precision measurements of detected anomalies to help in evaluating the nature of the defect and extent of the damage. The signals generated in the sensors by the flux leakage from an anomaly, however, are generally weak and can easily be obscured by spurious signals from the regular, i.e., non-anomalous, magnetic pattern. Moreover, maintaining the calibration of the inspection apparatus sufficiently well for absolute measurements throughout the course of an inspection has turned out to be troublesome.

Typical approaches to quantitative measurements in the past have relied instead on comparison of the measured response with the results of an essentially identical measurement on a specially prepared calibration specimen formed of a known material and containing magnetic anomalies of known features. Here the inspection instrument is calibrated (usually before each inspection session) with a specimen containing magnetic anomalies with features bracketing those expected in the material being evaluated. This procedure imposes a practical limitation in applying the magnetic flux leakage technique. A concomitant drawback is the cost in time, material, and handling associated with purchasing and maintaining a set of calibration specimens and performing the frequent calibration operations. To avoid these problems, magnetic flux leakage inspection apparatus has sometimes merely been used for preliminary screening to locate magnetic anomalies of possible significance. The located anomalies have then been subjected to a more accurate, but more time-consuming ultrasonic mapping technique to determine their characteristics for purposes of assessing the damage to the tank bottom.

Similar problems also arise in inspecting pipe and tubing used in the drilling, completion and production of oil and gas wells. Here strings of tubular sections are connected together to form an extended length for such purposes as drilling, casing, or transmission between the well head and a downhole location. The tubing is subject to much the same sort of mechanical damage or corrosion pitting as the storage tanks discussed above. Magnetic flux leakage techniques have been applied here too for the detection and evaluation of magnetic anomalies indicative of such damage and are disclosed, for example, in U.S. Pat. No. 4,704,580 of Moake et al. and U.S. Pat. No. 4,710,712 of Bradfield et al.

SUMMARY OF THE INVENTION

The present invention provides improvements to magnetic flux leakage inspection apparatus that permit more accurate measurements to be made in the field more conveniently with little or no increase in cost over prior art systems. The improved accuracy achievable with the invention permits quantitative anomaly measurements to be made in the field without the customary reliance on specially calibrated comparison specimens.

As in conventional magnetic flux leakage inspection systems, apparatus according to the invention includes a magnet and a sensor assembly. The magnet is disposed over a surface of a magnetizable material under inspection for inducing magnetic flux in the material, and the sensor assembly is disposed in a predetermined inspection position over the surface for detecting magnetic flux leakage from the material that may indicate a magnetic anomaly in the material. The magnet and sensor assembly are moved along over the surface, or alternatively the surface such as the surface of a length of tubing is moved along beneath the magnet and sensor assembly, while the sensor assembly scans for magnetic leakage flux. In the present invention the sensor assembly is formed with one or more independently suspended sensor blocks, each block including a plurality of sensors rigidly held in the block for detecting magnetic flux leakage. Each sensor block is independently mounted to permit the block to move perpendicular to the surface under inspection during the course of measurement as the sensor assembly and the surface are moved in scanning relation to one another. In particular to permit accurate measurement of magnetic flux leakage indicative of magnetic anomalies without contamination of the measurement results by the substantially larger flux leakage components that are normally present, each block is subject to stringent constraints on the permitted departures of the perpendicular movement from perpendicularity, that is, on the amount by which the block may tilt as it undergoes its perpendicular movement. Each of the one or more blocks may be disposed to ride on the surface of the material under inspection, and each block may then undergo perpendicular movement independent of any other block in response to variations of the surface encountered in the course of inspection without causing undesirable magnetic field components to be mixed into the detected signal that would otherwise mask the much weaker desired signal indicative of magnetic anomalies. With the sensor blocks resting on the surface or at least in the very close proximity of the surface under inspection, the sensors are positioned where the anomalous flux leakage is strongest, thereby providing for more accurate field determinations. In addition, irregularities or undulations in the surface produce less overall variation in the measured field on the average because individual sensor blocks move perpendicularly as needed to clear only the surface irregularities immediately underneath each individual block so that the sensor assembly as a whole conforms better to the shape of the surface than has been achieved in prior inspection apparatus.

Because a sensor assembly according to the invention is able to make more precise flux leakage measurements, the sensor assembly is able to take advantage of a significantly higher linear sensor density than that used in prior art magnetic flux leakage inspection apparatus. This permits finer spatial resolutions to be achieved. In one aspect of the invention the greater measurement accuracy achievable with precision perpendicularly movable sensor blocks makes it practicable to employ a two-dimensional array of sensors in a sensor block for achieving even greater spatial resolutions at higher inspection speeds.

In addition to improving upon the performance of existing instruments in fields where magnetic flux leakage measurements have regularly been used, the invention makes it practical to extend the use of magnetic flux leakage techniques to fields which have not used magnetic flux leakage measurements typically because the use of calibration specimens has not been possible or has been too costly or too slow. For example, apparatus according to the present invention may be used in the inspection of electric resistance welded, small diameter, coiled tubing which is produced in long continuous lengths (in excess of several thousand feet) at rates of hundreds of feet per minute. Current methods only permit a limited inspection of the weld line whereas the present invention provides for high-resolution and comparatively low-cost inspection of the entire surface.

A major problem introduced in instruments of the prior art when the sensors are allowed some freedom of movement that is overcome in the present invention is the tendency of the sensors to rotate. Extremely small rotations can inadvertently mix a small portion of the potentially very large horizontal magnetic field component with the vertical component being measured for purposes of characterizing the magnetic anomaly. This potentially large and unknown contribution to the measured response can produce major errors in interpretation. The prior art has largely avoided this problem by using rigidly supported sensor arrays. The present invention overcomes the motion and signal mixing problems to a practical degree, allowing a significant advance in the performance of magnetic flux leakage measurements.

In summary, the magnetic flux leakage sensor arrangement of the present invention brings the sensors closer to the surface than is practical using prior art instruments and so produces smaller signal changes in the presence of instrument motion over uneven surfaces than is possible in the prior art. The practical effect is that any given magnetic anomaly will produce both a larger signal than in a prior art instrument as well as a signal that varies less when surface unevenness is present with the result that smaller anomalies may be detected, more detailed information about the characteristics of the anomalies may be obtained, thicker materials may be probed for anomalies, and generally finer measurement resolutions may be obtained. Moreover, the need for collections of calibration or comparison specimens is avoided resulting in savings of cost and inspection time.

Other aspects, advantages, and novel features of the invention are described below or will be readily apparent to those skilled in the art from the following specifications and drawings of illustrative embodiments.

DETAILED DESCRIPTION OF ILLUSTRATIVE EMBODIMENTS

Magnetic flux leakage inspection apparatus according to the invention is illustrated here in an embodiment intended for use in inspecting chemical and petroleum storage tank bottoms. The invention may also be embodied in other forms of apparatus used in other environments for inspecting other forms of magnetizable materials. The invention is thus not to be limited to the specific embodiment disclosed here, which is offered only by way of example.

Figure 1:
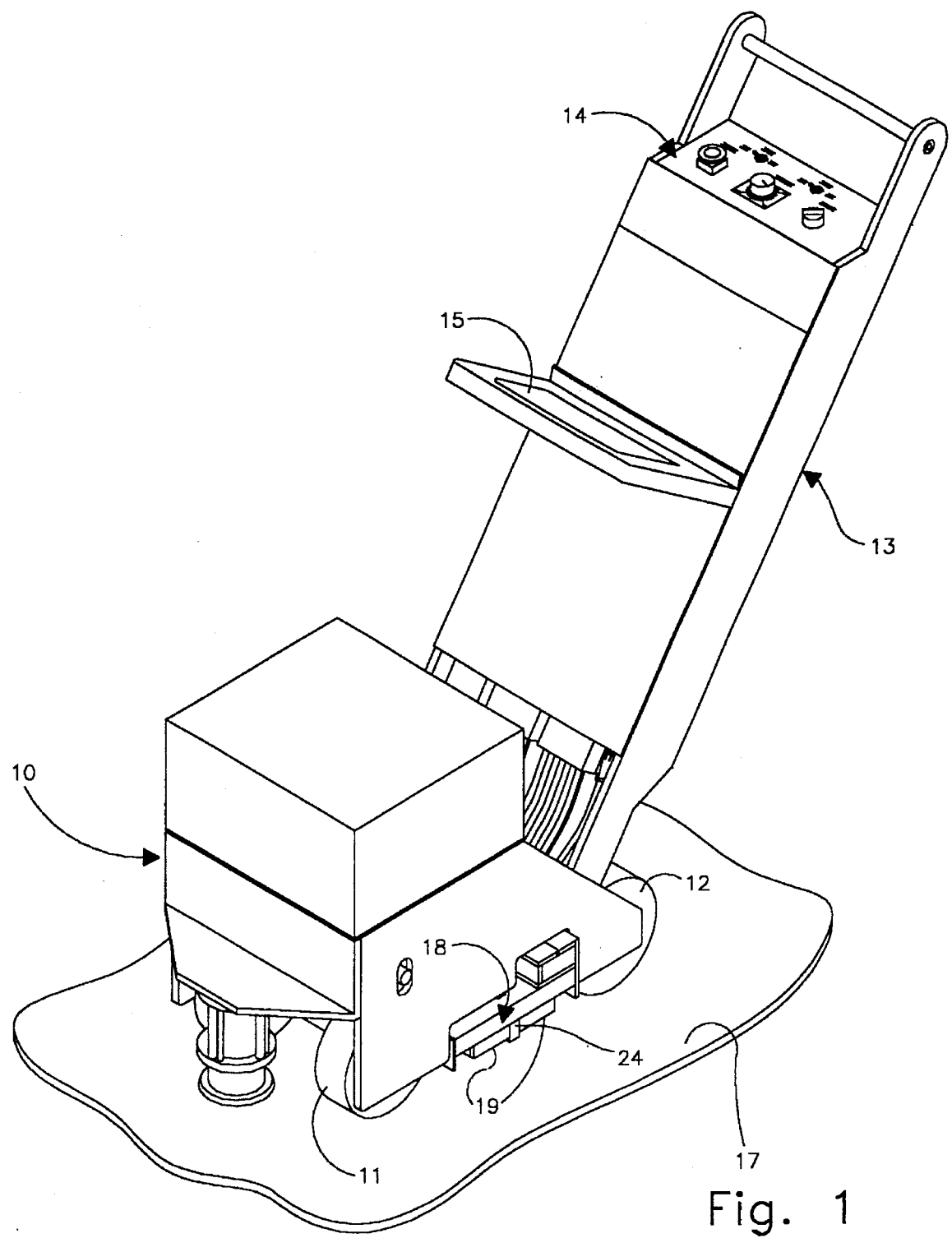
FIG. 1 is a perspective view of an embodiment of magnetic inspection apparatus including the invention.

An overall view of magnetic flux leakage inspection apparatus for inspecting a storage tank bottom is shown in FIG. 1. The apparatus includes a carriage assembly 10, which houses instrumentation for performing the flux leakage measurements. Carriage assembly 10 is mounted on wheels 11 and 12 so that it may be advanced over the surface under inspection, and the apparatus includes a handle portion 13 for an operator to steer and manipulate the apparatus over the surface. Mounted on handle portion 13 are control panel 14 for controlling the electronic and motorized or other powered operation of the apparatus and display screen 15 for displaying inspection results and instructions and for generally communicating with the operator. The apparatus is shown positioned on a portion of a plate 17, which is under inspection. Plate 17 is composed of course of a magnetizable material and for storage tank bottoms will generally be a ferromagnetic steel plate.

Figure 2:
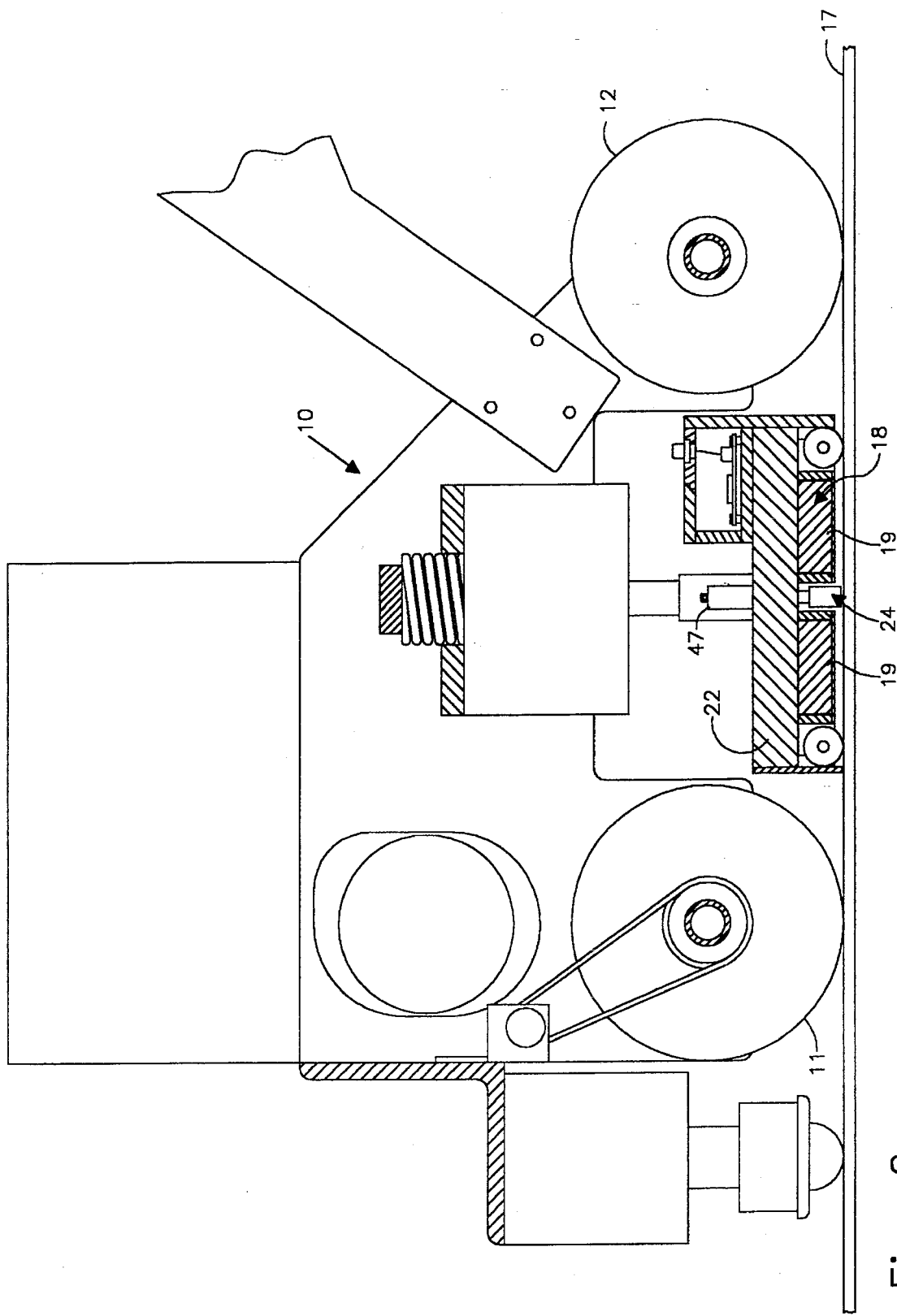
FIG. 2 is a side elevational view, partly in section, of the lower portion of the apparatus of FIG. 1.
Figure 3:
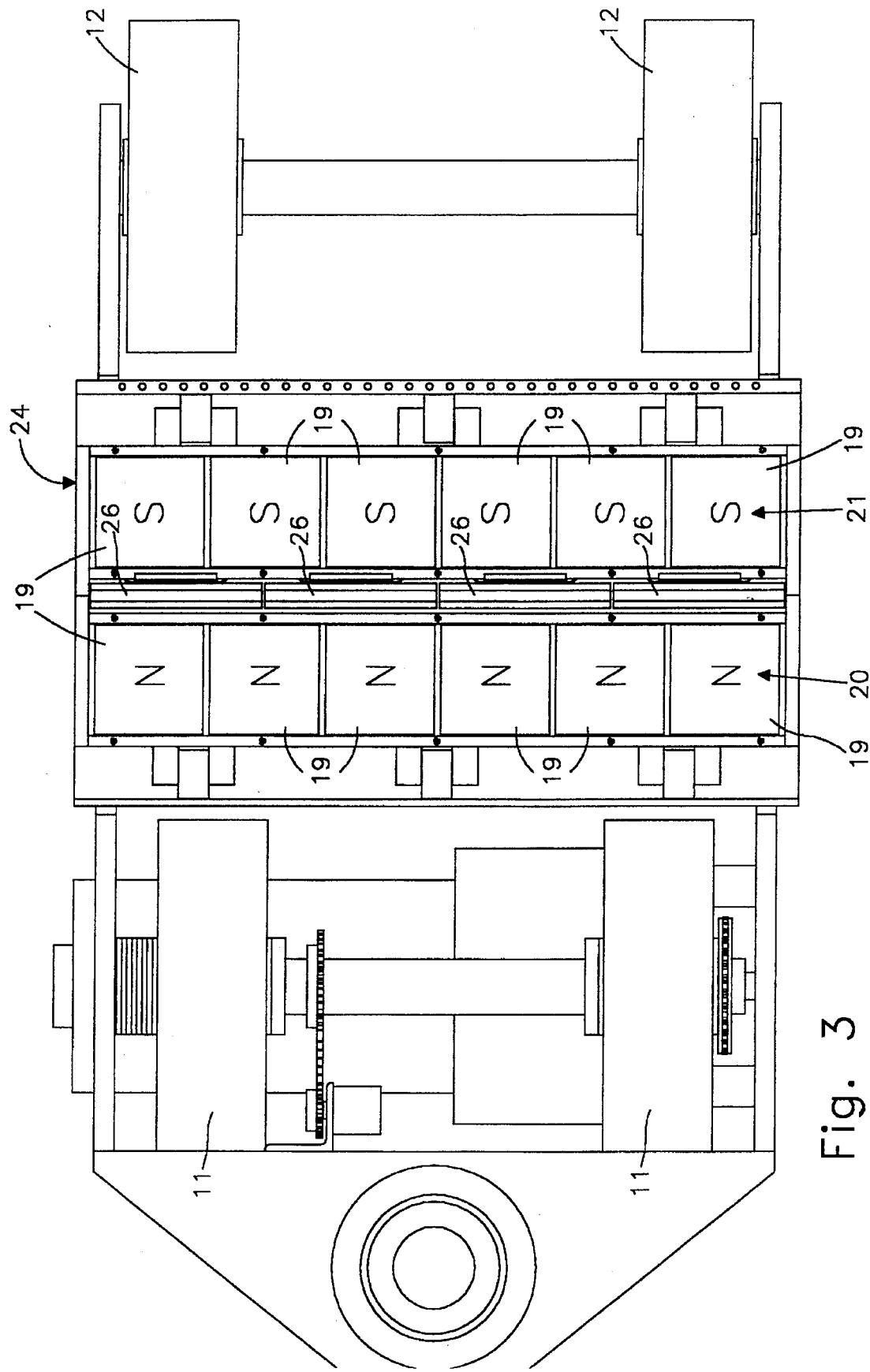
FIG. 3 is a bottom plan view of the apparatus of FIGS. 1 and 2.
Figure 4:
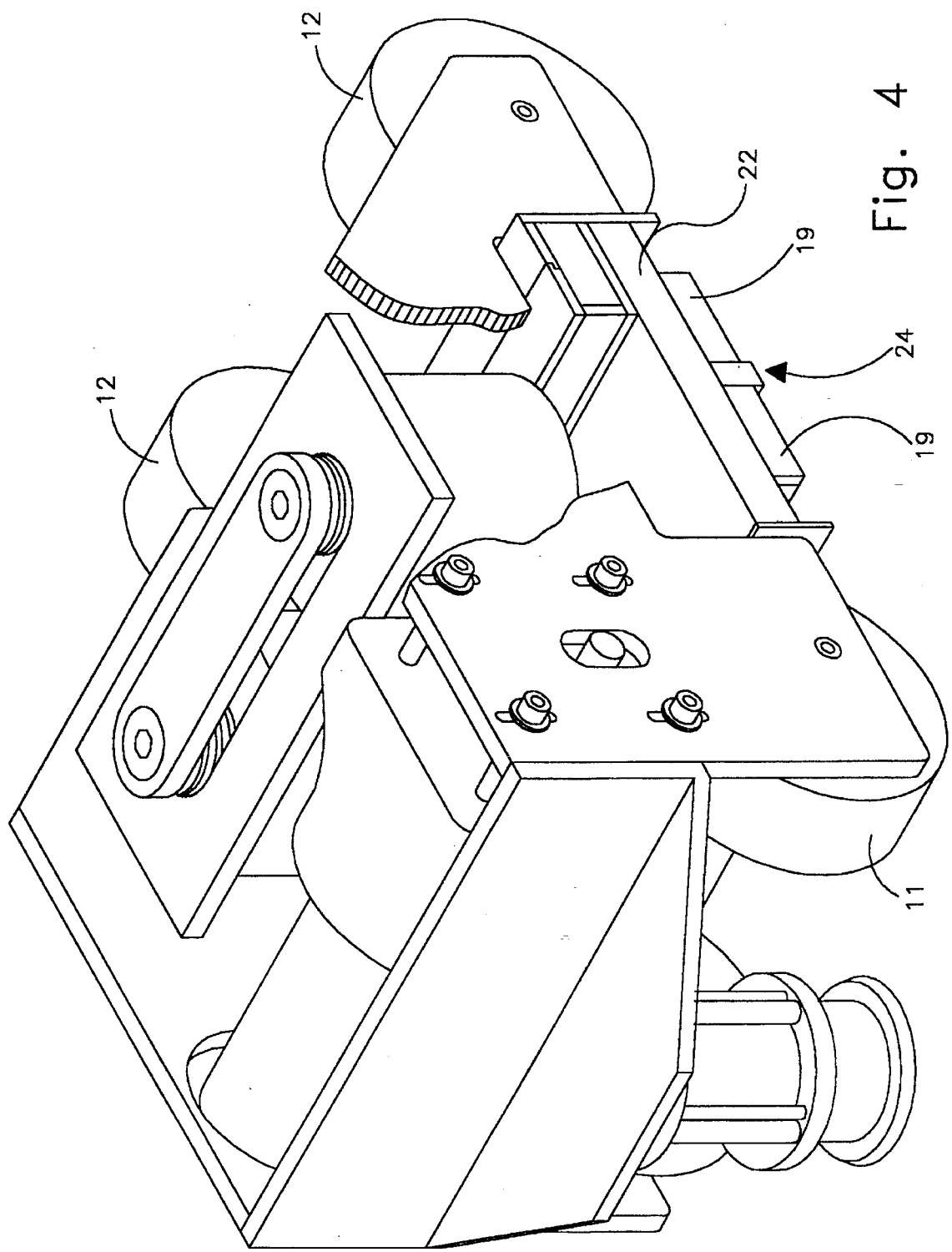
FIG. 4 is a perspective view, partially cut away, of a carriage assembly of the inspection apparatus of FIGS. 2 and 3.

Carriage assembly 10 includes a scan bar assembly 18 (see FIGS. 2 and 3) that includes a plurality of magnets 19 for inducing magnetization of plate 17 under inspection. The magnet configuration illustrated here provides two rows of permanent magnets 19 forming rows of north and south pole faces 20 and 21, respectively. The individual magnets 19 are magnetically coupled to one another through backing iron 22. When the pole faces of magnets 19 are magnetically coupled to plate 17, a continuous magnetic circuit is formed. Positioned between the poles 20 and 21 and forming a part of scan bar assembly 18 is a magnetic sensor assembly 24, which is used to detect magnetic leakage flux indicative of underlying magnetic anomalies associated with corrosive pitting and other plate damage. Other scan bar configurations of permanent magnets and electromagnets for providing the induced magnetization in the sample under inspection are known and may also be used with the present invention, which is not intended to be limited to the specific configuration illustrated here.

Figure 5:
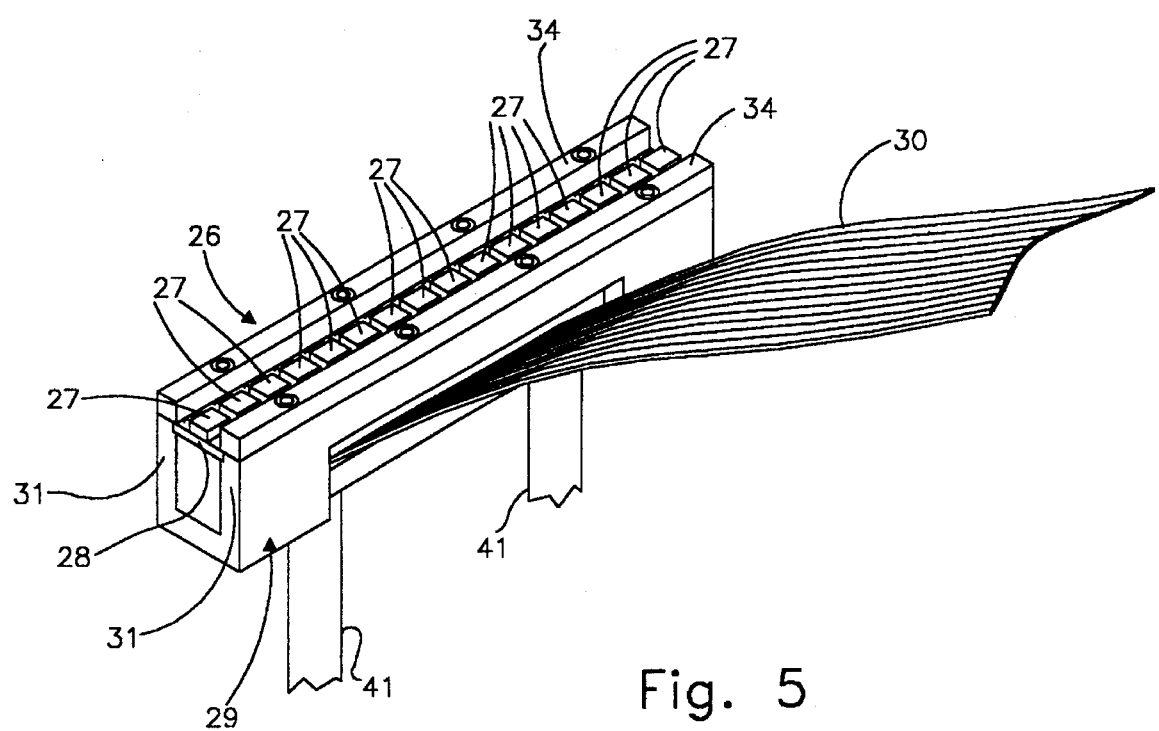
FIG. 5 is a perspective view of a sensor block according to the invention.

In the illustrated embodiment magnetic sensor assembly 24 includes a plurality of separate sensor blocks 26, each block being supported independently and each block being free to move up and down perpendicularly to the surface of plate 17. Each block 26 includes a plurality of sensors 27 for detecting the magnetic field at the sensor location. In the present embodiment sensors 27 are provided by Hall effect sensors although other sensors known to those skilled in the art may also be used. Within each block 26 the sensors 27 are rigidly mounted on a printed circuit board 28 that is itself rigidly held within the sensor block. The sensor block shown in FIG. 5 is formed with a metal channel-shaped framework 29 to provide structural integrity. Printed circuit board 28 is mounted across the channel arms 31 and is held securely in place by an epoxy filling 32 or similar potting compound in the channel of framework 29. A side of channel-shaped framework 29 is formed with an opening through which extends a ribbon cable 30 for making electrical connection with sensors 27. Covering bottom face of the printed circuit board and sensors is a protective sacrificial wear structure 33 for engaging the surface of the plate 17. Wear structure 33 is formed of a pair of protective strips 34 affixed to the edges of channel arms 31 so as to hold the printed circuit board in place and a thin sacrificial epoxy layer 36 covering the printed circuit board, sensors and strips 34. Strips 34 need protrude only to the level of sensors 27 or slightly beyond. The sensors are thus set off from the contact surface of sacrificial layer 36 only by the thickness of the sacrificial layer, which may be made quite thin and still provide protection for the sensors. During an inspection run sacrificial layer 36 is intended to ride on the surface of plate 17 so that in this way the sensors may be brought in as close as practically feasible to the surface of the plate under inspection. The present invention anticipates surface wear and other damage to the sensor blocks 26, and so the blocks are designed for easy and economical replacement on a regular basis.

As a sensor block 26 rides on the surface of plate 17, it will typically encounter an uneven surface. Even though plate 17 is nominally flat, it will nevertheless exhibit small departures from uniform flatness due in part to debris, such as scale or oily and gritty deposits, that have accumulated on the surface and in part to undulations or other imperfections or distortions in the shape of the surface itself. In flux leakage inspection apparatus of the prior art this problem has been avoided simply by mounting the magnetic sensor assembly so that when the sensors are in their inspection position they have sufficient clearance to avoid such irregularities. As a result the sensors in prior art apparatus have been spaced farther from the surface under inspection than in the present invention. While the greater spacing found in prior art apparatus provides sufficient clearance to avoid disruptive and damaging collisions with the sensors, it also positions the sensors in a weaker part of the magnetic anomaly field, which diminishes in strength as one moves away from the surface under inspection. Even a small displacement of the sensors away from the surface results in a noticeably weaker signal being generated within the sensors.

In the present invention a sensor block 26 is able to ride directly on the surface under inspection because the block is mounted for movement perpendicular to the surface during the course of an inspection run without disrupting the collection of data. As surface irregularities due to accumulated debris or surface undulations are encountered, the individual sensor blocks 26 ride up and down over the irregularities, while the apparatus continues to read the sensors. A distinction is made here between the relatively small irregularities in the surface due to debris or surface undulations and larger surface discrepancies due to plate welds, for example. Apparatus is known that enables the sensors, and typically the entire scan bar assembly, to be displaced away from the surface under inspection when a plate weld or other such large-scale discrepancy is encountered, but the sensors are not intended to collect meaningful data while such movement is taking place. In the present invention it has been discovered, however, that meaningful data may be collected, even permitting quantitative determinations of magnetic anomaly structure, if the sensor block is constrained within stringent limits not to tilt as the block undergoes its perpendicular movement responding to irregularities in the surface.

In the embodiment disclosed here sensor block 26 is provided with a pair of supporting members in the form of elongate posts 41 that have bearing surfaces 42 for facilitating the perpendicular movement. The bearing surface may be formed, for example, simply by machining the post with sufficient precision to provide a smooth, sliding fit. Alternatively, a separate bearing material may be applied to the post or an air bearing may be employed. The structure and formation of bearing surfaces is a well developed art and further details of bearing construction need not be given here. Posts 41 are fixed perpendicular to framework 29 on the top side of the sensor block so as to be parallel to one another to within 0.02 radians. Scan bar assembly 18 includes a receiving member provided here by backing iron 22 which is formed with a pair of elongate bores 43 for snugly receiving posts 41 and engaging bearing surfaces 42. Although posts 41 and elongate bores 42 are illustrated here with circular cross section, they may of course have other cross sectional shapes. For example, in some applications it may be preferable to use only a single supporting member to support each sensor block. This may be the case, for example, when inspecting tubing where the sensor blocks are supported over the cylindrical surface of tubing by a single elongate member aligned to move along a radius of the tubing and hence perpendicular to the cylindrical surface. In such an application it may be desirable for the supporting member to take the shape of an elongate post with square cross section to prevent rotational movement about the longitudinal axis of the elongate post.

Figure 6:
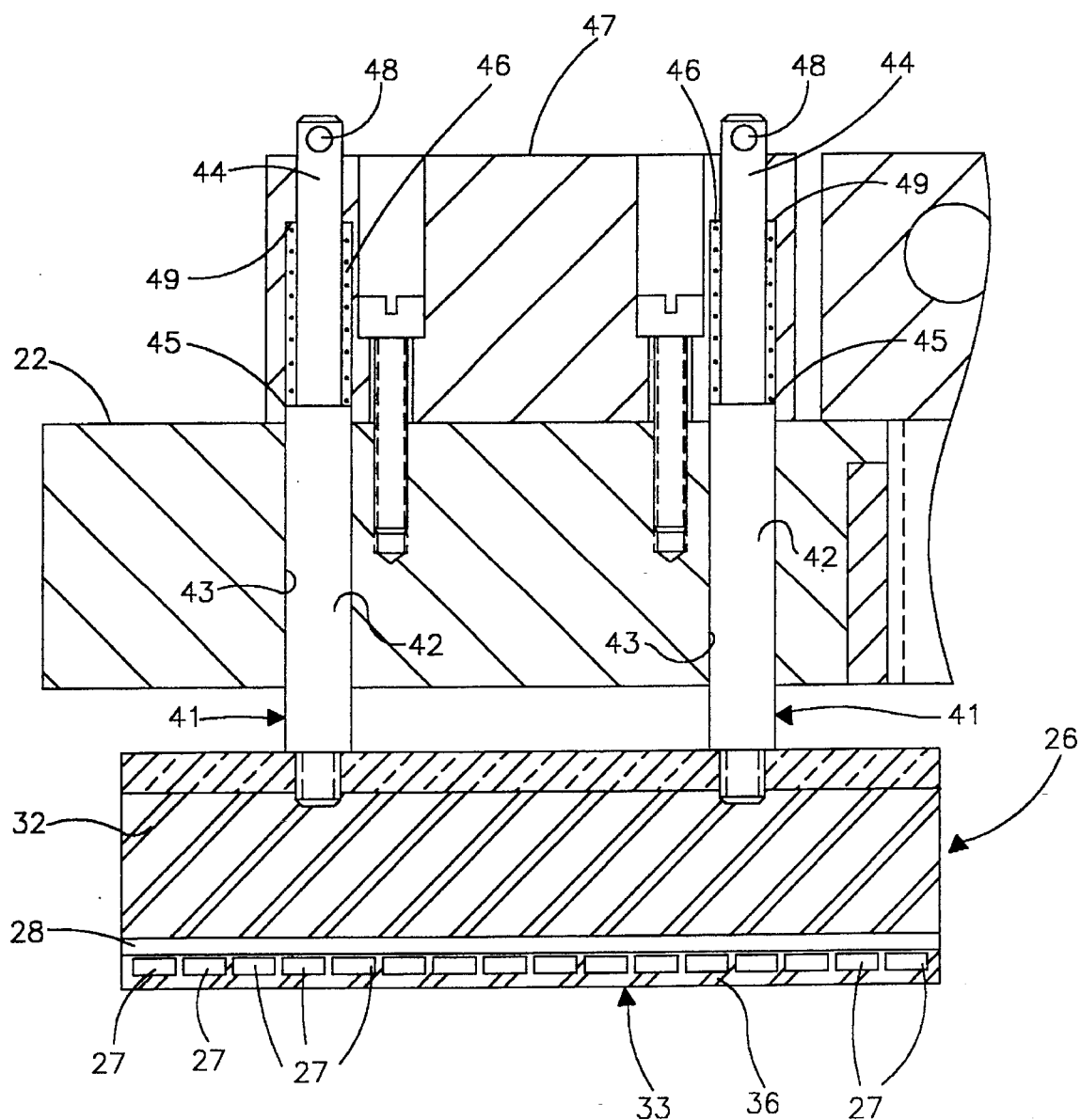
FIG. 6 is a cross-sectional view showing the sensor block of FIG. 5 and its mounting in the scan bar assembly.

As illustrated in FIG. 6 each post 41 is formed with a larger diameter portion that carries bearing surface 42 and that meets with a smaller diameter portion 44 at shoulder 45. A compression spring 46 is coiled around the smaller diameter portion 44. Each bore 43 extends into the top frame member 47 of scan bar assembly 18 and the associated post 41 extends through frame member 47 where it is held in the assembly by pin 48. The portion of bore 43 in frame member 47 is provided with a shoulder 49 for receiving one end of spring 46. Spring 46 presses against shoulders 45 and 49 and thereby urges sensor block 26 against the surface of plate 17 to maintain contact between the plate and sacrificial wear layer 36.

As indicated above, it is important that each sensor block 26 be constrained to undergo its perpendicular movement with minimal tilt. If block 26 rotates too much, the sensors will be caused to receive large extraneous signals that complicate if not completely obscure the interpretation of an anomaly signal. The effect of a small sensor rotation may be appreciated as follows. For a plate 17 that is free of defects, hence free of magnetic anomalies, the induced magnetization in the region between pole faces 20 and 21 is parallel to the surface of the plate. The field in this region is largely confined to the plate itself, but it extends to some degree to the space above the plate. Although the field strength above the plate and between the pole faces is notably weaker than the field strength within the plate, it is nevertheless non-negligible compared with the typical field strength associated with a magnetic anomaly. As a sensor block rotates, the sensors will detect a contribution from the parallel, non-anomalous field. Even a relatively small rotation of the sensor block causes a significant fraction of the relatively large horizontal component of the magnetic field to be mixed with the normally much smaller perpendicular component of the magnetic field at the sensor. It has been discovered that these contributions are the source of significant noise in the detected signal and can be removed as an obstacle to quantitative measurements by controlling the amount of permissible tilt. Thus, for example, it has been discovered that meaningful measurements can be made if the permissible tilt of a sensor block as it undergoes its perpendicular movement is limited substantially to at most 0.02 radians. With the surface-responsive sensor block construction disclosed here and this limitation on the permissible tilt, stronger magnets may be used, which may be deployed closer to the plate under investigation, which provides stronger anomaly signals, With the improved measurement accuracy achievable here, a significantly higher linear sensor density and a significantly smaller information sampling grid may be used than is commonly found in on-site flux leakage inspection apparatus of the prior art. More closely spaced sensors 27 are able to discern smaller spatial changes in the flux leakage signal than sensors that are more widely spaced. A magnetic anomaly produces a signal that has both transverse and longitudinal spatial extent. "Longitudinal" refers here to the direction of travel of the sensor blocks (i.e., of the inspection apparatus) over the surface under inspection (or equivalently of the surface under the sensor blocks), and "transverse" refers here to the direction parallel to the line formed by the sensors, which is generally but not necessarily perpendicular to the direction of travel. Magnetic anomalies of larger physical extent in the longitudinal and transverse directions produce signals or responses having a larger spatial extent, and deeper magnetic anomalies produce larger signals than shallower anomalies. A magnetic anomaly of a given size and shape will produce a larger and narrower signal if it is on the nearer surface to the sensors as opposed to being located on the farther surface. To reduce the critical dependency on instrument calibration, it is desirable that sensors 27 be spaced sufficiently close together that there is less than a 3 db variation in response to the smallest depth and volume loss that it makes practical sense to detect and assess (i.e., to determine its size and shape) regardless of where the anomaly occurs with respect to the sensor positions. For example, in the assessment of chemical and petroleum storage vessels, inspection apparatus is generally expected to detect and size a flat-bottomed hole that is ⅛ inch in diameter and extends 20% through the material in question. Most vessel material in current use is between 0.25 and 0.50 inches in thickness. Such a ⅛ inch diameter hole in a plate 0.25 inches thick produces a signal having a −3 db width of about 0.4 inches if it is on the far surface and about 0.25 inches if it is on the near surface. An effective sensor spacing of 0.4 inches enables the apparatus to detect the presence of a randomly positioned ⅛-inch diameter anomaly. At this sensor spacing, however, sizing accuracy is greatly diminished. An effective sensor spacing of 0.2 inches provides that material anomalies in the far surface can be sized with better than 30% (3 db) accuracy regardless of where the anomaly is placed with respect to the sensors. In the present apparatus this accuracy may be obtained even when the anomaly is placed randomly on the surface.

Figure 7A:
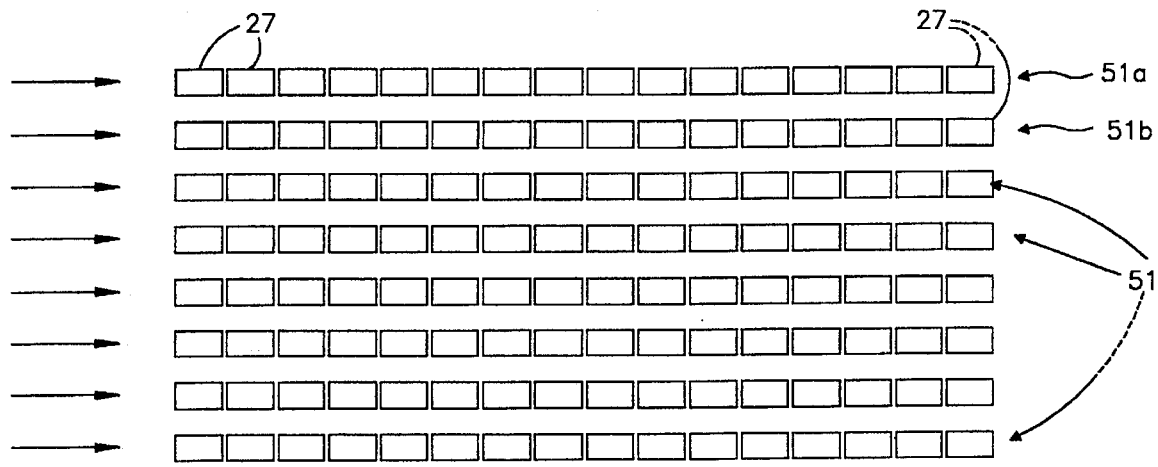
FIGS. 7A and 7B are diagrammatic plan views of alternative two-dimensional sensor array patterns for use with the invention.
Figure 7B:
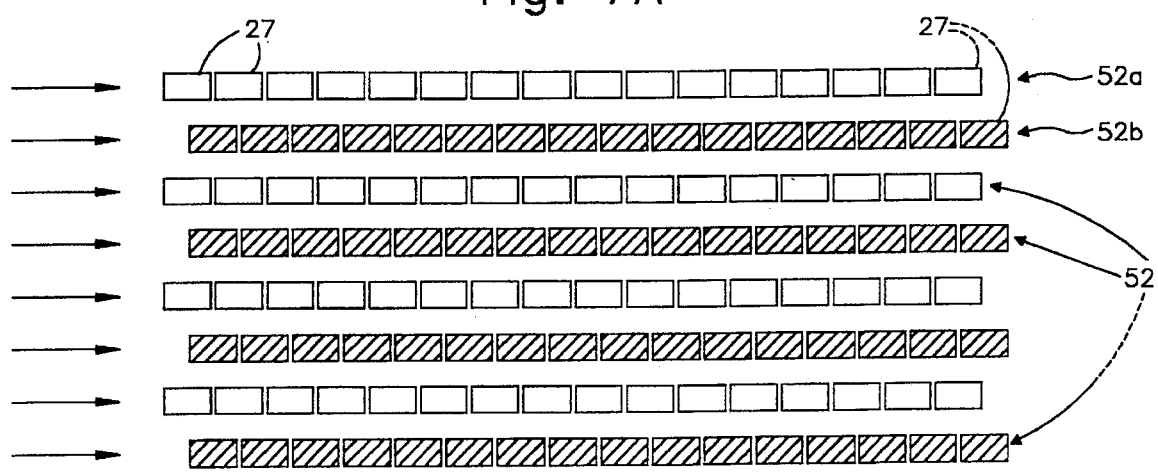

With the improved sensitivity achieved here the apparatus may take advantage of two-dimensional sensor arrays on sensor blocks 26. FIGS. 7A and 7B show two alternative arrays of parallel rows that may be scanned in parallel in the direction of the arrows. The pattern of FIG. 7A is formed by a plurality of parallel rows 51 of sensors 27 with the sensors in adjacent rows such as rows 51a and 51b lining up with one another. In the pattern of FIG. 7B the sensors are disposed in a plurality of parallel rows 52 with the sensors in adjacent rows such as rows 52a and 52b being offset from one another. Two-dimensional array patterns such as these permit greater scanning speeds. The offset array pattern of FIG. 7B in addition defines a differently shaped grid of image points that is better suited to obtaining greater resolution, although greater demands will generally be made on the data processing to achieve this. Capture and transfer of data in such two-dimensional blocks provides for significantly faster scanning and subsequent processing. On-site flux leakage inspection apparatus of the prior art, however, has not had the quantitative measurement capability needed to sufficiently distinguish such two-dimensional block data patterns and take advantage of block data capture.

Because of the improved accuracy and resolution achievable here, special calibration specimens for individual anomaly types are no longer needed. Instead, most of the calibration of the instrument may be performed at the time of manufacture prior to use by the end user. The instrument parameters that influence the translation of a signal measurement or signal profile into a quantitative description of a magnetic anomaly may readily be determined through laboratory measurements on magnetic anomalies of known characteristics. Instead of using on-site calibration specimens as in the prior art, calibration curves for various separation distances and anomaly sizes may be supplied with the instrument normally included with the system software for operation of the instrument. The only necessary user calibrations relate to a one-time calibration each time the instrument (i.e., the sensor array) is placed on a test object. In practice, this calibration may be performed automatically by the on-board computer during the system setup procedure. This field calibration is needed to normalize the measured response to the actual material being tested as any particular magnetic plate may have slightly different magnetic properties. The magnet separation distance, which is generally needed for such field calibrations, can be measured by techniques that are well known and need not be disclosed in any detail here. Through the field calibration the instrument may be programmed to self-adjust to changing conditions whenever regions free from magnetic anomalies are available for evaluation. The instrument software may be configured to determine the presence of such conditions automatically.

In summary, mounting the sensors 27 in a plurality of blocks achieves several important advantages. First, any localized scale or surface debris that lifts one block leaves the others unaffected. Second, this mounting procedure permits each block to contact the surface of plate 17 with a light rubbing contact so that the surface-sensor separation distance is kept as small as possible. This, in turn, means that the measurement system always produces the largest possible signals because sensor signals increase as the surface-sensor separation distance decreases.

Quantitative flux leakage inspection apparatus according to the invention may be applied in new areas previously unsuited to such measurements because very fine spatial resolution is required or the use of calibration specimens is not feasible in practice. One such example is the inspection of electric resistance welded, small-diameter coiled tubing, which is produced in long continuous lengths typically in excess of several thousand feet at rates of hundreds of feet per minute. Application of magnetic flux leakage inspection apparatus according to the present invention enables high-resolution inspection of the entire surface, and not just of the weld line as is commonly done in current methods.

The above descriptions and drawings disclose illustrative embodiments of the invention. Given the benefit of this disclosure, those skilled in the art will appreciate that various modifications, alternate constructions, and equivalents may also be employed to achieve the advantages of the invention. Therefore, the invention is not to be limited to the above description and illustrations, but is defined by the appended claims.

What is claimed is:

1. Magnetic flux leakage inspection apparatus for precision inspection of a magnetizable material for magnetic anomalies, said apparatus including magnetizing means disposed over a surface of said material for inducing magnetic flux in said material for inspection thereof, and a sensor assembly disposed in a predetermined inspection position for detecting magnetic flux leakage from said material indicative of magnetic anomalies in the material, wherein said magnetizing means, said sensor assembly, and said material are disposed for relative movement of said magnetizing means and said sensor assembly in said predetermined inspection position along said surface for inspection of said material, said apparatus being characterized in that said sensor assembly comprises:

a sensor block including a plurality of sensors rigidly held therein for detecting
said magnetic flux leakage,
said sensor block being disposed in said inspection position to ride substantially on said surface, and
said sensor block being mounted for movement perpendicular to said surface in response to variations of said surface encountered in the course of inspection, wherein said sensor block is mounted to undergo said perpendicular movement through a distance of at least twice a characteristic size of said variations, and wherein said block is constrained to tilt at most 0.02 radians during said perpendicular movement;
whereby said sensor block undergoes perpendicular movement in response to said variations without causing a significant contribution to be mixed in from a magnetic field component parallel to the surface under inspection.

2. The apparatus of claim 1, further comprising at least one supporting member fixed to said sensor block and presenting a bearing surface for facilitating said perpendicular movement, and a receiving member formed to receive said supporting member and engage said bearing surface to permit said perpendicular movement.

3. The apparatus of claim 2 wherein said supporting member comprises a first elongate post secured at one end to said sensor block and having a bearing surface, and said receiving means defines a first elongate bore formed to receive said first post and engage said bearing surface to permit longitudinal movement of said first post therein and thereby to effect said perpendicular movement.

4. The apparatus of claim 3 wherein said plurality of sensors are disposed in a two-dimensional array comprising a plurality of parallel rows of sensors wherein the sensors in adjacent rows are in line with one another.

5. The apparatus of claim 3 wherein said plurality of sensors are disposed in a two-dimensional array comprising a plurality of parallel rows of sensors wherein the sensors in at least two adjacent rows are offset from one another.

6. The apparatus of claim 3, further comprising a second said post secured to said sensor block and parallel to said first post, and said receiving means defines a second elongate bore parallel to said first bore and formed to receive said second post to permit longitudinal movement of said second post therein.

7. The apparatus of claim 2 wherein said sensor block further comprises means defining a sacrificial wear surface formed for engaging the surface of the material under inspection.

8. The apparatus of claim 1 wherein said plurality of sensors are disposed in a line with said sensors being spaced apart from one another by a separation no greater than 0.40 inch.

9. The apparatus of claim 1 wherein said plurality of sensors are disposed in a two-dimensional array comprising a plurality of parallel rows of sensors wherein the sensors in adjacent rows are in line with one another.

10. The apparatus of claim 1 wherein said plurality of sensors are disposed in a two-dimensional array comprising a plurality of parallel rows of sensors wherein the sensors in at least two adjacent rows are offset from one another.

11. The apparatus of claim 1, further comprising means for urging said sensor block against the surface of said magnetizable material under inspection.

12. Magnetic flux leakage inspection apparatus for precision inspection of a magnetizable material for magnetic anomalies, said apparatus including magnetizing means disposed over a surface of said material for inducing magnetic flux in said material for inspection thereof, and a sensor assembly disposed in a predetermined inspection position for detecting magnetic flux leakage from said material indicative of magnetic anomalies in the material, wherein said magnetizing means, said sensor assembly, and said material are disposed for relative movement of said magnetizing means and said sensor assembly in said predetermined inspection position along said surface for inspection of said material, said apparatus being characterized in that said sensor assembly comprises:

a plurality of independently suspended sensor blocks, each said sensor block including a plurality of sensors rigidly held therein for detecting said magnetic flux leakage, each said sensor block being disposed in said inspection position to ride on said surface, and each said sensor block being mounted for movement perpendicular to said surface in response to variations of said surface encountered in the course of inspection independently of the other sensor blocks of said plurality, wherein each said sensor block is mounted to undergo said perpendicular movement through a distance of at least twice a characteristic size of said variations, and wherein each said block is constrained to tilt at most 0.02 radians during said perpendicular movement;

whereby said sensor blocks undergo independent perpendicular movement in response to said variations without causing a significant contribution to be mixed in from a magnetic field component parallel to the surface under inspection.

13. The apparatus of claim 12 wherein said plurality of sensor blocks are disposed in a line side by side with one another.

14. The apparatus of claim 13, further comprising at least one supporting member for each said sensor block, each said supporting member being fixed to a respective said sensor block and presenting a bearing surface for facilitating perpendicular movement of said respective sensor block, and a receiving member formed to receive said supporting members and engage said bearing surfaces to permit said perpendicular movement.

15. The apparatus of claim 14 wherein each said supporting member comprises a first elongate post secured at one end to said respective sensor block and having a bearing surface, and said receiving means defines a first plurality of bores formed to receive the first posts of said supporting members and engage said bearing surfaces to permit longitudinal movement of said first posts therein and thereby to effect said perpendicular movement.

16. The apparatus of claim 15 wherein said plurality of sensors are disposed in a two-dimensional array comprising a plurality of parallel rows of sensors wherein the sensors in adjacent rows are in line with one another.

17. The apparatus of claim 15 wherein said plurality of sensors are disposed in a two-dimensional array comprising a plurality of parallel rows of sensors wherein the sensors in at least two adjacent rows are offset from one another.

18. The apparatus of claim 15, further comprising a second said elongate post for each said sensor block, each said second post being secured to a respective said sensor block and parallel to said first post, and said receiving means defines a second plurality of elongate bores parallel to said first plurality of bores and formed to receive said second posts to permit longitudinal movement of said second post therein.

19. The apparatus of claim 13 wherein said sensor block further comprises means defining a sacrificial wear surface formed for engaging the surface of the material under inspection.

20. The apparatus of claim 12 wherein the plurality of sensors in each said sensor block are disposed in a line with said sensors being spaced apart from one another by a separation no greater than 0.40 inch.

21. The apparatus of claim 12 wherein said plurality of sensors of each said sensor block are disposed in a two-dimensional array comprising a plurality of parallel rows of sensors wherein the sensors in adjacent rows are in line with one another.

22. The apparatus of claim 12 wherein said plurality of sensors of each said sensor block are disposed in a two-dimensional array comprising a plurality of parallel rows of sensors wherein the sensors in at least two adjacent rows are offset from one another.

23. A sensor block for use with magnetic flux leakage inspection apparatus for precision inspection of a magnetizable material for magnetic anomalies, said inspection apparatus including magnetizing means disposed over a surface of said material for inducing magnetic flux in said material for inspection thereof, and a sensor assembly for detecting magnetic flux leakage from said material indicative of magnetic anomalies in the material, said sensor assembly including sensor block mounting means for mounting said sensor block, wherein said sensor block comprises:

a housing;

a plurality of sensors rigidly held in said housing for detecting said magnetic flux leakage; and first and second elongate posts, each said post being secured at one end to said housing and being formed with a bearing surface to be received in said sensor block mounting means to permit longitudinal movement of said first and second posts in said sensor block mounting means, wherein said first and second posts are parallel to one another to within 0.02 radians for facilitating movement of said housing with respect to said sensor block mounting means in a direction perpendicular to said surface.

24. The apparatus of claim 23, further comprising a spring disposed for urging said sensor block toward said surface when said sensor block is received in said sensor block mounting means.

* * * * *